US007618374B2

(12) United States Patent
Barnes et al.

(10) Patent No.: US 7,618,374 B2
(45) Date of Patent: Nov. 17, 2009

(54) IMAGE PLANE SENSING METHODS AND SYSTEMS FOR INTRA-PATIENT PROBES

(75) Inventors: Stephen R. Barnes, Bellevue, WA (US); Mirsaid Bolorforosh, Portola Valley, CA (US); Vaughn R. Marian, Saratoga, CA (US); David I. Bruce, Lafayette, CA (US); Tim Thigpen, Portland, OR (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 775 days.

(21) Appl. No.: 10/951,970

(22) Filed: Sep. 27, 2004
(Under 37 CFR 1.47)

(65) Prior Publication Data
US 2006/0074319 A1    Apr. 6, 2006

(51) Int. Cl.
*A61B 8/14* (2006.01)
(52) U.S. Cl. ............... 600/466; 600/424; 600/438; 600/462; 600/467; 600/471; 607/122
(58) Field of Classification Search ........... 600/407, 600/424, 437, 438, 459, 462, 464, 466, 467, 600/471, 373; 607/122
See application file for complete search history.

(56) References Cited

U.S. PATENT DOCUMENTS

| | | | | |
|---|---|---|---|---|
| 5,391,199 A | * | 2/1995 | Ben-Haim | 607/122 |
| 5,398,691 A | * | 3/1995 | Martin et al. | 600/463 |
| 5,830,145 A | | 11/1998 | Tenhoff | |
| 5,840,031 A | * | 11/1998 | Crowley | 600/440 |
| 5,876,345 A | | 3/1999 | Eaton et al. | |
| 5,879,305 A | | 3/1999 | Yock et al. | |
| 6,027,451 A | * | 2/2000 | McGee et al. | 600/463 |
| 6,045,508 A | * | 4/2000 | Hossack et al. | 600/447 |
| 6,171,303 B1 | * | 1/2001 | Ben-Haim et al. | 606/15 |

(Continued)

OTHER PUBLICATIONS

"Realtime Position Management™ Integrating Advanced Mapping, Navigation and EP Recording," property of Boston Scientific Corporation or its affiliates; www.bostonscientific.com; 3 pgs.; 2003.

(Continued)

*Primary Examiner*—Brian Casler
*Assistant Examiner*—Amanda L. Lauritzen

(57) ABSTRACT

A position of an imaging plane relative to a catheter or other probe is aligned with tissue of interest. Ultrasound tissue images may be registered to the catheter position with minimal rotational ambiguity. The spatial position of an ablation catheter or other device with respect to the imaging plane is more accurately determined, allowing a physician to identify specific anatomy in the relative location of a catheter or catheters. Another alternative or additional approach to determining the position of an imaging plane is to determine the relative position of two or more catheters. A catheter associated with imaging is then moved or bent in a direction having a known spatial relationship with the imaging plane. The position of the catheter is relative to each is then determined again to determine the angle or position of the imaging plane. In addition or as an alternative to determining an angular position of an imaging plane relative to a catheter, an ultrasound image of tissue is generated with acoustic elements for position identification. The acoustic elements are used as an imaging transducer array as well as devices for determining relative positions of the catheters.

10 Claims, 3 Drawing Sheets

U.S. PATENT DOCUMENTS

| | | |
|---|---|---|
| 6,216,027 B1 | 4/2001 | Willis et al. |
| 6,259,941 B1 * | 7/2001 | Chia et al. .................. 600/424 |
| 6,266,552 B1 * | 7/2001 | Slettenmark ................ 600/424 |
| 6,332,089 B1 * | 12/2001 | Acker et al. ................ 600/424 |
| 6,490,474 B1 | 12/2002 | Willis et al. |
| 6,514,249 B1 * | 2/2003 | Maguire et al. ............... 606/41 |
| 6,587,709 B2 * | 7/2003 | Solf et al. ................... 600/424 |
| 6,612,992 B1 | 9/2003 | Hossack et al. |
| 6,690,963 B2 * | 2/2004 | Ben-Haim et al. .......... 600/424 |
| 6,755,791 B2 * | 6/2004 | Kawashima ................ 600/467 |
| 7,019,650 B2 * | 3/2006 | Volpi et al. ................ 340/572.1 |
| 7,158,754 B2 * | 1/2007 | Anderson .................. 455/41.1 |

OTHER PUBLICATIONS

"RPM Realtime Position Management™ System," on Boston Scientific Website www.bostonscientific.com/med; printed on Sep. 9, 2004; 2 pgs.; 2004.

* cited by examiner

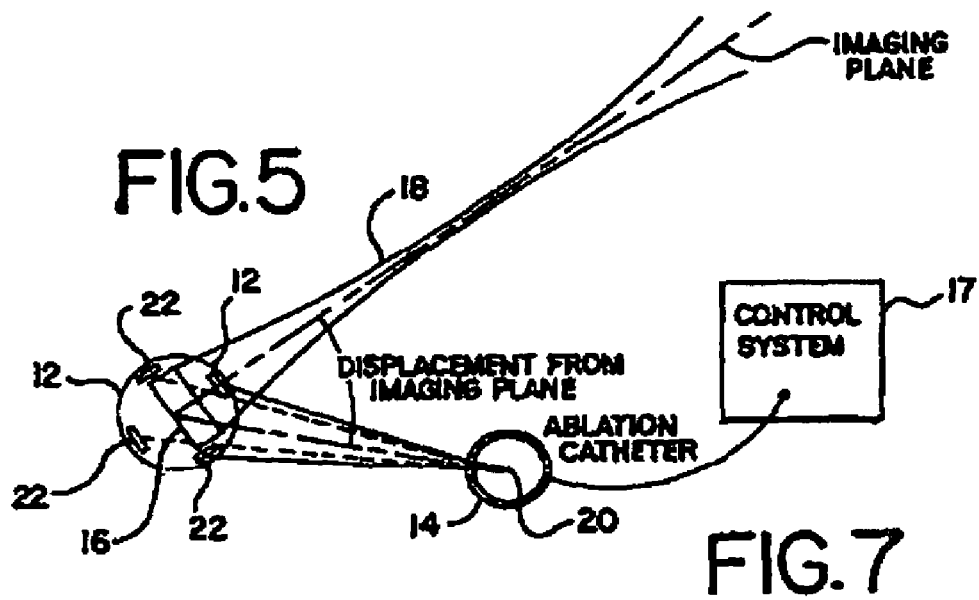
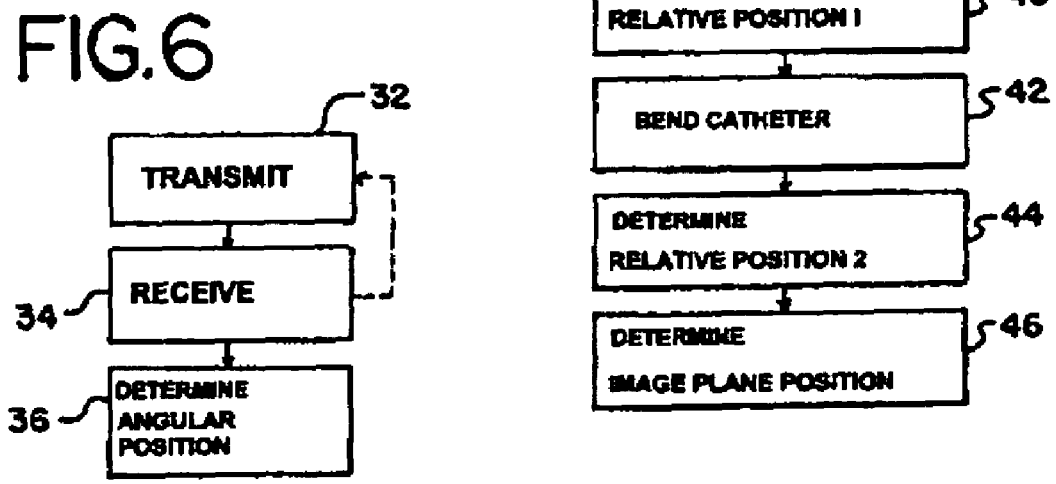
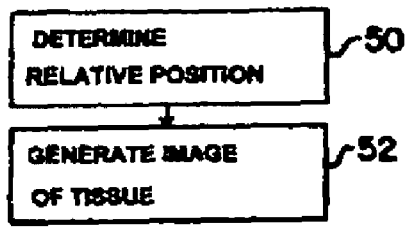
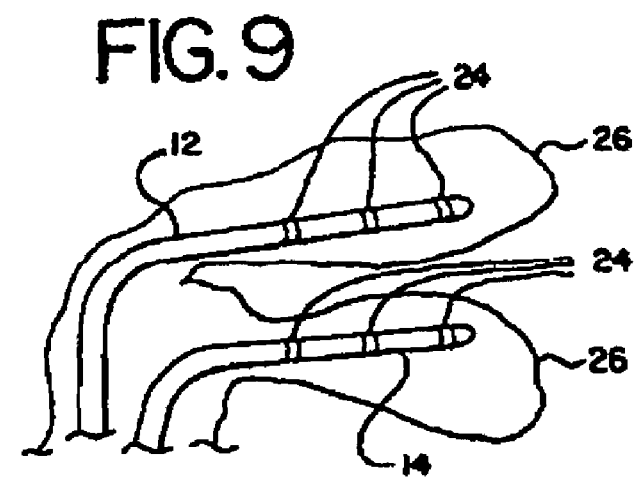

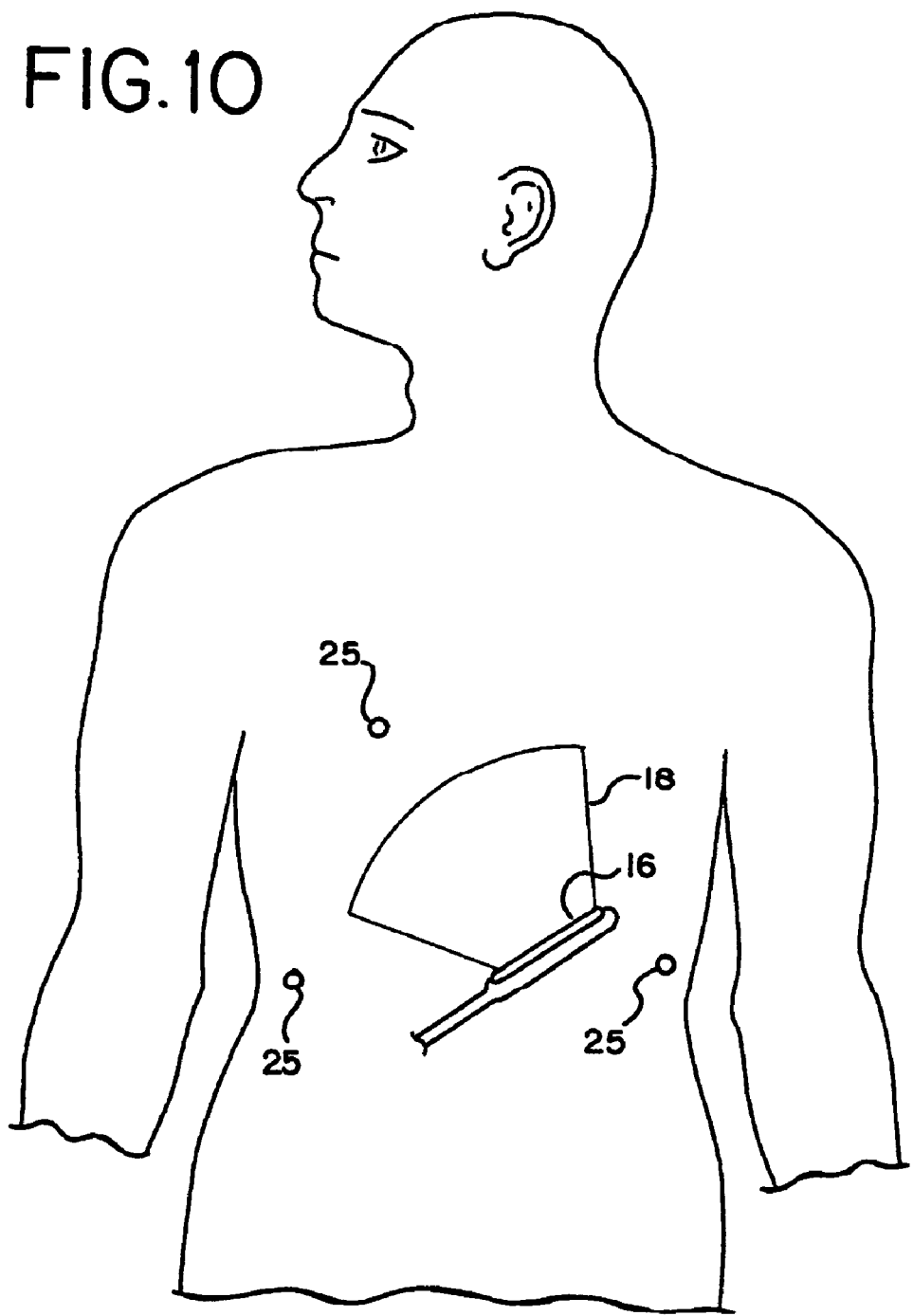

US 7,618,374 B2

IMAGE PLANE SENSING METHODS AND SYSTEMS FOR INTRA-PATIENT PROBES

BACKGROUND

The present invention relates to determining positions of intra-patient probes. In particular, the position of an intra-patient probe, such as a catheter, is determined relative to another catheter or tissue for imaging.

Successful intra-cardiac or surgical procedures require accurate information about the spatial position of the surgical or other devices with respect to anatomy. For example, during radiofrequency ablation procedures, knowing the position of the ablation device is important. Radiofrequency electrical ablation is performed on the conduction pathways adjacent to the pulmonary artery. The ablation is performed inside the ventricle as high up on the conduction pathway as possible while avoiding ablating the inside of the pulmonary artery.

Accurate placement of the ablation catheter for performing the ablation may be obtained using visualization. Fluoroscopy can be used to visualize a projection siluette of a catheter and anatomy. The dimensions and distances along the projection direction cannot be seen using fluoroscopy. Minimized exposure to X-rays performed during fluoroscopy imaging may also be desired.

U.S. pat. No. 6,490,474 avoids the use of X-ray radiation to determine the position of catheters. The relative position of multiple catheters is visualized using ultrasound transducers. The transducers are spaced along each of two or more catheters. Ultrasonic time-of-flight is used to identify the relative spatial locations of the transducers. The relative transducer locations, the known mechanical properties of the catheters and the positioning along the catheters allow the relative trajectories of the catheter bodies to be predicted. However, identifying the relative position of two or more catheters does not in itself visualize the anatomy and, even if one of the catheters is a catheter probe for imaging, the method may not provide sufficient information.

BRIEF SUMMARY

By way of introduction, the preferred embodiments described below include methods and systems for determining a position of an imaging plane. To assist with aligning a surgical device in one probe for operating or examining tissue, another probe scans a region. The position of the scanned region relative to the catheter with the transducer array and/or the surgical device is used for feedback to image the desired tissue and to place the surgical device in the desired position relative to the tissue. For example, a first catheter position relative to the imaging plane of a second catheter probe for imaging is determined. A position of an imaging plane relative to a catheter or other probe is aligned with tissue of interest. The spatial position of an ablation catheter or other device with respect to the imaging plane is more accurately determined, allowing a physician to identify specific anatomy in the relative vicinity of a catheter or catheters. Another alternative or additional approach to determining the position of an imaging plane of a catheter probe is to determine the relative position of two or more catheters. The catheter associated with imaging is then moved or bent in a direction having a known spatial relationship with the imaging plane. The position of the catheter relative to each is then determined again, allowing one to determine the angle or position of the imaging plane. In addition or as an alternative to determining an angular position of an imaging plane relative to a catheter, an ultrasound image of tissue is generated with acoustic elements for catheter position finding. The acoustic elements are used as a sparse random imaging array as well as devices for determining relative positions of the catheters.

In a first aspect, a system is provided for determining a position of an imaging plane relative to a catheter. A catheter with an ultrasound imaging array has a corresponding imaging plane. Another catheter has an antenna, such as an electromagnetic antenna or an ultrasound element. Two catheters are at least in part different. A processor is operable to determine the angular position of the imaging plane relative to the first catheter as a function of a signal of the first antenna.

In a second aspect, a method is provided for determining a position of an imaging plane within a patient. A transmission is performed from an intra-patient probe. A signal is received at a different intra-patient probe in response to the transmission. An angular position of an imaging plane of a transducer array of one of the two intra-patient probes is determined as a function of the signal.

In a third aspect, a method is provided for using position information for imaging. The relative positions of two or more catheters are determined with different groups of acoustic elements on the different catheters. An ultrasound image of tissue is also generated with these same different groups of acoustic elements as a function of the determined relative position.

In a fourth aspect, a method for determining a position of an imaging plane relative to a catheter is provided. A relative position of at least two catheters with different groups of acoustic elements is determined. One of the catheters has an acoustic imaging transducer array. The catheter with the acoustic imaging transducer array is bent. The determination of the relative positions is then repeated. The position of the imaging plane is determined as a function of the different relative positions determined prior to and after the bending.

The present invention is defined by the following claims, and nothing in this section should be taken as limitation on those claims. Further aspects and advantages of the invention are disclosed below in conjunction with the preferred embodiments.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

FIG. 5 is a cross-sectional diagram of the systems of FIGS. 1A and B using radiofrequency identification devices;

FIG. 6 is a flow chart diagram of one embodiment of a method for determining angular position of an imaging plane;

FIG. 7 is a flow chart of another embodiment of a method for determining an angular position of an imaging plane;

FIG. 8 is a flow chart of one embodiment of a method for generating an image of tissue;

FIG. 9 is a graphical representation of one embodiment of a plurality of intra-patient probes with antennas used for both position determination and imaging; and FIG. 10 is a graphical representation of one embodiment of an intra-patient probe with antennas on the skin of a patient for position determination.

DETAILED DESCRIPTION OF THE DRAWINGS AND PRESENTLY PREFERRED EMBODIMENTS

The spatial position of an invasive surgical device with respect to an imaging plane imaging tissue is detected. By calculating the position of the imaging plane with respect to the surgical device, the position of the surgical device is determined relative to the tissue. Using transmission and reception between a device and an ultrasound imaging intra-patient or catheter transducer array allows positioning of the imaging plane relative to the device. By providing position sensing devices on a catheter or other probe with an ultrasound imaging array, the angular position of the imaging plane is determined.

Different methods and systems may be used for determining the imaging plane angular position. One or more antennas may be provided in a same catheter or probe as an ultrasound imaging transducer. Acoustic, RF, magnetic or other antennas may be provided. Time-of-flight, signal strength or frequency is used to identify an angular position of a transmitter or receiver relative to the antennas. By positioning the transmitter or receiver on a different device, such a different catheter, the position of the imaging plane relative to the other device is provided. Alternatively or additionally, the relative positions of two or more catheters are determined. A catheter associated with an imaging array is bent in a particular direction relative to the imaging array, such as bending the tip of a catheter towards an imaging plane. The relative positions of the catheters are determined again. The change in the relative positions based on the known bending direction indicates the position of the imaging plane relative to the catheter.

Where a plurality of acoustic elements are used to determine the relative positions of two or more catheters or probes, the same elements may be used as part of an imaging array. For acoustic imaging, time-of-flight delays applied to different elements within an array allow formation of an acoustic image. By determining the relative positions of different transducers spaced along a plurality of catheters, corresponding time-of-flight information may be calculated. Signals from the various transducers may then be used to generate an image of tissue using the calculated time-of-flight information.

Figure 1A:
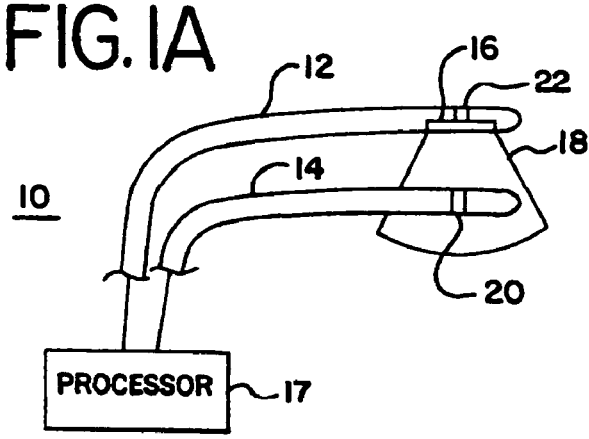
FIGS. 1A and 1B are two different views of an embodiment of a system for determining a position of an imaging plane relative to a catheter or intra-patient probe.
Figure 1B:
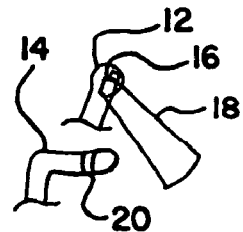

One or more of the various aspects described above may be implemented in a given system. FIGS. 1A and 1B show one embodiment of a system 10 for determining a position of an imaging plane relative to a probe. The system 10 includes at least two probes 12, 14 and a processor 17. Additional, different or fewer components may be provided, such as providing additional probes or an ultrasound imaging system.

The probe 12 is an intra-patient probe or catheter. For example, the probe 12 is an intra-cardiac probe or catheter less than 10 millimeters, such as being about 8 or 10 French in diameter. In alternative embodiments, the probe 12 is an endocavity probe, such as a transesophageal probe, or an intra-operative probe. The probe 12 includes an ultrasound transducer array 16.

The transducer array 16 is a one-dimensional linear array, but multidimensional arrays, curved arrays or combinations thereof may be used. The array 16 is positioned in parallel to a longitudinal axis of the probe 12. Alternatively, the array 16 is positioned to extend perpendicular to the longitudinal axis, such as circling around a portion or an entire circumference of the probe 12. The transducer array 16 may alternatively be positioned on the tip portion of the probe 12. The imaging plane 18 corresponds to the transducer array 16. The transducer array 16 may be a phased array for performing sector or Vector circular scanning imaging plane. Alternatively, a linear format scan is provided for the imaging plane 18. Where the transducer array 16 is a one-dimensional array, a mechanical elevation focus or no elevation focus may be provided, and an electrical azimuth and range focus is provided. Since the transducer array 16 is fixed relative to the probe 12, the imaging plane 18 extends at a particular angular orientation from the probe 12. For example and as shown in FIG. 1B, the imaging plane 18 extends away from another probe 14. Since the probe 12 may be rotated, the imaging plane 18 may also rotate within the patient. In alternative embodiments, the transducer array 16 may be moved or repositioned within the probe 12 without rotating the probe 12.

The probe 14 is a catheter or intra-patient probe, such as one of the probes or catheters described above for the probe 12. In one embodiment, the probe 14 includes a surgical device, such as an ablation electrode for radio frequency ablation. Alternatively or additionally, the probe 14 includes ports or tools for surgery, cutting, threading, stitching, injecting or other surgical procedures. While the probe 14 may be the same as the probe 12, the probe 14 is alternatively a different probe than the probe 12. For example, the probe 14 has a different size, different tools, different components, or other difference in arrangement, configuration or operation. While shown as completely separate devices in FIGS. 1A and 1B, the probes 12 and 14 may be conjoined or connected together, such as the probe 14 extending through a port in a portion of the probe 12 or vice versa. A same or different guiding catheter may be used for each of the probes 12, 14. The probes 12, 14 are then positioned in different positions for at least a part of or the entire extent of the probes 12, 14.

The probe 14 includes an antenna 20. Antenna as used herein is a device for transmitting or receiving signals of various types, such as radio frequency, ultrasound or other signals. The antenna 20 is an acoustic element, such as a PZT, composite PZT or micro-electromechanical transducer. Radio frequency antennas, such as a radio frequency transponder, RF transmitter, RF receiver, or RF transceiver, may be used. For radio frequency implementation, the antenna 20 is an electrode, wire or other antenna structure for transmitting digital or analog information, such as transmitting a carrier wave encoded with digital information or transmitting an analog pulse without encoding. The antenna 20 acts as a single point source, but may have a less distributed or more restrictive radiation pattern. While one antenna 20 is shown in FIGS. 1A and 1B, additional of the same or different antennas may be provided in a similar or different locations along the probe 14. In one embodiment, the antenna 20 is positioned adjacent to an ablation coil or other implement of the probe 14 to be placed in a particular location.

Other probes, such as providing for a total of three or more probes, may be provided in alternative embodiments. Each additional probe includes a transducer imaging array, an antenna, or combinations thereof. The probes may be the same or different than either of the probes 12, 14 described above.

The probe 12 with the ultrasound transducer array 16 also includes an antenna 22. The antenna 22 is an acoustic, radio frequency or other antenna, such as a same antenna as described above for the antenna 20. The antenna 22 is positioned relative to the ultrasound imaging array 16. In one embodiment, the antenna 22 is positioned at a fixed relationship relative to the transducer array 16, such as adjacent to, formed on a same substrate, within the same probe 12, with an overlapping lateral extent as the array 16, or spaced from the array 16 at a known location.

The antenna 22 is distributed or formed to provide angular information relative to the transducer array 16. FIGS. 2 through 5 show different embodiments of the antenna 22 for determining an angular relationship of the transducer array 16 to the antenna 20 or the probe 14. The spatial orientation of the imaging plane 18, the antenna 20, and the ultrasound transducer array 16 relative to tissue and each other are aligned to view and act on the tissue. By determining the relative position such as the angular position of the imaging plane, more accurate, efficient or rapid alignment may be provided.

Figure 2:
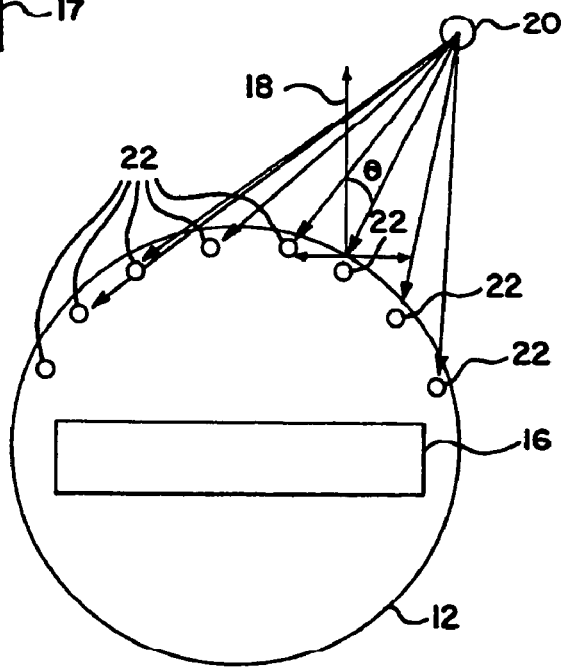
FIG. 2 is a cross-sectional diagram showing one embodiment of an arrangement of antennas associated with an imaging transducer.

FIG. 2 shows the antenna 22 including a plurality of elements, such as acoustic transducers. The acoustic elements as the antennas 22 are separate from the ultrasound imaging transducer array 16. In one embodiment, the antennas 22 are separate from the imaging array 16 while being integrated on a same substrate. For example, the transducer array 16 is formed with half lambda or lambda spacing of micro-electromechanical membrane elements. Micro-electromechanical membranes are formed on the same substrate but different from the membranes used for the array 16 to act as the antennas 22. The same or different structures, such as the size of the membrane, may be used for the elements of the array 16 than for the antennas 22. In an alternative embodiment, the antennas 22 are formed as separate substrates or separate devices than the array 16.

The antennas 22 are positioned at different locations around the circumference of the probe 12. While shown as a semicircle around the circumference in FIG. 2, the antennas 22 may be positioned around the entire circumference, to a greater extent or to a lesser extent than shown in FIG. 2. The antennas 22 are positioned on a same position along the lateral axis of the probe 12, but may be positioned at different locations along the axis in alternative embodiments. A single ring or multiple rings of elements or antennas 22 are provided.

Figure 3:
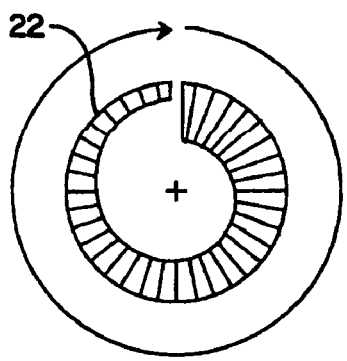
FIG. 3 is a cross-sectional diagram of one embodiment of a catheter with an antenna.

FIG. 3 shows another embodiment of the antenna 22. A single antenna or a plurality of antennas is arranged around the circumference to provide a variable thickness antenna 22, such as a maximum thickness at one portion of the circumference and extending about 360 degrees to a narrowest portion. The thickness of the antenna 22 varies as a function of the angle around the catheter probe 12. In one embodiment, the antenna 22 is a ring or piezoelectric cylinder with electrodes on the inside and outside surfaces relative to the surface of the probe 12. The piezoelectric is polled in the radial direction. Composite ceramics may additionally be used. The antenna 22 has an cylinder axis of the internal surface that is parallel to but not linear to the axis of the external surface of the cylinder or probe 12, causing the cylinder wall thickness to vary as a function of angular position. This gives a different frequency response at each position around its circumference. In the orthogonal direction, i.e. in and out of the plane of FIG. 3, the dimension is short relative to a wavelength and thus is omni-directional in this direction.

Figure 4:
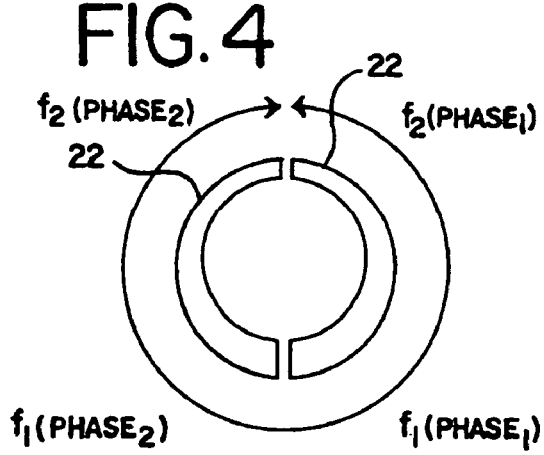
FIG. 4 is a cross-sectional diagram of another embodiment of a catheter with two antennas.

FIG. 4 shows an alternative embodiment with an antenna 22 that has a variable thickness as a function of angle. Two or more antennas 22 have a variable width along the radius or diameter as a function of angle or position along the circumference. Each of the antennas 22 curves as a function of length along the antenna 22 or circumference. While shown as having small and large ends that are the adjacent and the same, different relative sizes may be provided. The large end of one antenna 22 may match with the small end of the other antenna in alternative embodiments. The antennas 22 are positioned in a same plane, such as orthogonal to or perpendicular to a longitudinal axis of the probe 12. In alternative embodiments, the antennas 22 are substantially in the same plane or in different planes.

FIG. 5 shows another embodiment where the antennas 22 are radio frequency identification devices, commonly known as RF-ID's. Each radio frequency identification device is a transponder operable to generate a coded signal in response to a remotely transmitted signal. In one embodiment, each of the radio frequency identification device antennas 22 is a semiconductor or micro-electromechanical device formed on a silicon or other semiconductor substrate, such as a same or different substrate used for forming the transducer array 16. One-dimensional, two-dimensional or three-dimensional antenna structures may be provided. As shown in FIG. 5, four radio frequency identification device antennas 22 are positioned around the circumference of the probe 12 relative to the transducer array 16. Three, five or more radio frequency identification device antennas may be used in other embodiments. Differences in spacing along the longitudinal axis of the probe 12 are also provided in other embodiments.

Referring to FIG. 1A, the system 10 includes the processor 17. The processor 17 is a general processor, digital signal processor, application specific integrated circuit, transmit beamformer, receive beamformer, control processor, field programmable gate array, analog circuit, digital circuit, combinations thereof or other now known or later developed devices for generating transmit signals for position finding and/or processing the received signals in response to the transmission. The processor 17 may include a plurality of devices distributed in different systems, such as a processor within an ultrasound imaging system operating in conjunction with a processor in a radio frequency ablation system. In another embodiment, the processor 17 is entirely within an ultrasound imaging system separate from other systems also connected to one of the probes 12, 14. In one embodiment, the processor 17 includes the components described in U.S. pat. No. 6,490,474, the disclosure of which is incorporated herein by reference, for determining relative spatial positions between different catheters.

The processor 17 is operable to determine angular position information of the imaging plane 18 relative to the probe 12 as a function of a signal from the antenna 20. The angular position information may include an angle away from scanning a particular reference point, such as the antenna 20, an absolute angle relative to the probe 12, a direction closest to positioning the imaging plane at the desired location, or other angle relative to an elevational axis of the transducer array and/or an angle around the circumference of the probe 12. The angular position of the imaging plane 18 relative to the other catheter 14 is determined directly or indirectly.

The processor 17 operates with the antenna 22 as a receive antenna and the antenna 20 as a transmit antenna. The angular position is determined as a function of the transmitted signal from antenna 20 and the responsive receive signal of the antenna 22. In an additional or alternative embodiment, the processor 17 determines the position in response to a transmit signal from the antenna 22 and receive signal from the antenna 20. By processing receive signals, the process is responsive to the transmission as well as the reception to determine an angular position. Alternatively, the processor 17 is responsive to both the transmission and reception by comparing the transmitted signal timing, strength or other characteristic relative to receive signal timing, strength or other characteristic, or any combination of these characteristics.

The processor 17 is free of signals from the ultrasound imaging array 16, but may alternatively receive signals from the ultrasound imaging array 16 for determining the position of the imaging plane 18. For example, at least one element of the ultrasound imaging transducer array 16 is connected with the processor 17. The position of the imaging plane 18 may be determined laterally as well as rotationally with respect to the probe 12 using the information from an element of the array 16 spaced laterally from the antenna 22. Alternatively, the antenna 22 includes a plurality of different antennas spaced laterally.

With the receive antennas 22 shown in FIG. 2, the processor 17 determines the angular position information of the imaging plane 18 relative to the antenna 20 as a function of the signals of the plurality of antennas 22 on the probe 12. The antennas 22 are either receive or transmit antennas in conjunction with the antenna 20 acting as a transmit or receive antenna. For example, the transmit antenna 20 outputs a short burst of acoustic signals. The transmitted signal is received by the antennas 22. Differences in the time-of-flight are then calculated. The time-of-flight information indicates the distance between the antenna 20 and each of the antennas 22. Using the angle between the imaging plane 18 and a line extending from the antenna 22 to the antenna 20 associated with the shortest time-of-flight, the angle between the imaging plane 18 and the other probe 14 is determined. Interpolation or extrapolation may be used to provide a line or angle between the probe 12 and the antenna 20 associated with the shortest time-of-flight, such as where the shortest distance is between antenna 20 and one of the antennas 22. The angle between the catheter position associated with the antenna 20 and the normal Vector to the ultrasound imaging transducer array 16 is calculated. As the surgeon or other operator changes the spatial position of either of the probes 12, 14 or an associated surgical instrument, the angular position of the imaging plane 18 may be adjusted in real time to provide exact placement of a surgical device, such as an ablation electrode.

In one embodiment, the energy transmitted between the antennas 22 and 20 is different than energy used for imaging with the ultrasound imaging transducer array 16, such as using RF energy or acoustic energy at different frequencies, different coding and/or with other different characteristics. The differences are used to avoid or minimize interference. In alternative embodiments, the processor 17 is synchronized with the imaging system transmit and receive beamformers to perform processing between the antennas 22 and 20 and the imaging with the transducer array 16 as a function of time.

For the embodiments shown in FIG. 3, the processor 17 is operable to determine the angular position information of the imaging plane 18 relative to the probe 12 as a function of frequency encoding. The frequency response of the antenna 22 varies as a function of location around the circumference or ring of the antenna 22. By transmitting a wide band signal or a signal with a frequency bandwidth similar to or wider than the frequency response of the antenna 22 shown in FIG. 3, the spectrum of the receive signal indicates the angle closest to the transmit antenna 20. The frequency associated with the maximum amplitude or the frequency with the least amplitude attenuation indicates the angle of the antenna 22 to the antenna 20. The known angular relationship of the transducer array 16 to the antenna 22 is then used to determine the relative position of the imaging plane 18. In an alternative embodiment, the antenna 22 is used to transmit a wide band signal. The spectrum received at the antenna 20 indicates the relative angles.

For the embodiment shown in FIG. 4, the same angular determination method is used, however, a right and left ambiguity may exist. Each of the antennas 22 indicates an angle based on frequency response. Using the antennas 22 as transmit antennas with different phases, such as zero and 180 degree relative phases, the left-right ambiguity may be mitigated. As another example, 90 degree phasing or clocking allows the two antennas 22 to operate as a quadrature pair to resolve the right-left ambiguity. The relative phasing indicates which signals are from which antenna 22. Relative timing or signal strength is used to indicate which of the two antennas 22 is closer to the antenna 20. The phasing encoding provides a dipole response about the cylinder axis or lateral axis of the probe 12, allowing the angle from one of the antennas 22 to be identified as being within one or the other sectors. More precise angular positioning may be inferred by amplitude response. By dividing the antennas into a plurality of antennas with relative clocking positions or phases, a narrower angle may be provided.

Referring to FIG. 5, the processor 17 is operable to determine the angular position information of the imaging plane 18 relative to the probe 12 as a function of signals from the multiple radio frequency identification devices 22. Signal strength and/or time-of-flight is used. The time interval between reception of an interrogation signal from the antenna 20 and the coded response may be different for each of the antennas 22. By generating interrogation signals at periodic intervals, the timing or signal strength of the coded responses indicate the location of the imaging plane 18 relative to the antenna 20. To minimize processing power, the signal strength of the coded response may be used. The antennas 22 output information at a different signal strength corresponding to the relative angle. A directional antenna, such as a micro-electromechanical antenna, is provided. For example, a one antenna 22 outputs or radiates energy in a generally 90 degree arch with more strength than the other 270 degrees. The angular displacement is then determined from the relative signal strength of the responses from the various antennas 22.

In yet another embodiment, the processor 17 is operable to determine the angular position information as a function of different positions of the probe 12 relative to the antenna 20. For example, a tip of the probe 12 includes an antenna 22. Where a control line, such as a steering wire, is provided in the probe 12 for bending the probe tip in a fixed direction relative to the imaging plane 18, a difference in position of the antenna 22 relative to the antenna 20 over time indicates the position of the imaging plane. The catheter is bendable in one or more specific directions, such as at an angle away from the imaging plane, or within the imaging plane. For example, the tip bends towards the imaging plane within the same or parallel plane. By identifying the location of the tip, then bending the tip towards the imaging plane, and identifying the location, the imaging plane position is determined relative to the antenna 20. Since the direction of the bend relative to the imaging plane 18 is known, the angular position of the imaging plane 18 and probe 12 relative to antenna 20 is determined. An alternative method for determining the axial orientation of the catheter 12 relative to the ablation catheter 20 would be to employee 2 different antennas 22 along the axis of the catheter 12. The antennas 22 are located in the same plane coaxial to the axis of the catheter 12. Relative signal strengths of their coded responses to an interrogation by the ablation catheter antenna 20 is used to infer the relative distances of each antenna 22 with respect to antenna 20. The processor 17 uses this information to determine the axial orientation of the catheter 12 relative to the transmitter antenna 20.

FIG. 6 shows one embodiment of a method for determining a position of an imaging plane relative to a probe. Additional, different or fewer acts may be provided. The method is implemented using the system 10 of FIGS. 1A and 1B or a different system.

In act 32, a signal is transmitted from an intra-patient probe. For example, an ultrasound signal having a short or long pulse duration is transmitted. As another example, a wide band pulse is transmitted. As yet another example, a coded interrogation signal is transmitted, such as a radio frequency interrogation signal. More than one signal may be transmitted, such as transmitting sequentially or from two or more antennas. The same signal or different signals are transmitted from each of the antennas, such as transmitting signals associated with different phasing. Signals may be transmitted from more than one probe or from only a single probe.

In act 34, a signal is received at a different intra-patient probe in response to the transmission from the first probe. For example, an ultrasound signal is received. In one embodiment, the ultrasound signals received by an element are transmitted from different elements or an array of transducer elements. In another embodiment, the receive ultrasound signal is received at a plurality of transducer elements. The signal is received with elements at a known spatial orientation relative to a transducer array. The elements for receiving the position determination signals may be the same or separate from the elements of the imaging transducer array.

For radio frequency information devices, the reception of a signal is part of the transponding from a plurality of different radio frequency identification devices on the probe. The receive signal is at the RFID or at the original transmitter. In another embodiment, the signal is received with an antenna having a variable width or other characteristic. The variable characteristics vary as a function of angle. A plurality of variable width or other variable characteristic antennas may be used to receive the same signal or different signals.

As indicated by the dashed line between acts 34 and 32, the transmit and receive process may be used for various combinations of the same or different elements at the same or different times. For example, one element may be used for transmitting at one time and receiving at a different time. As another example, a plurality of elements transmit at substantially the same time using different frequencies, coding or other characteristics to distinguish the signals. The reception of signals from a plurality of different transmitters may occur at a substantially the same time. The receive signals from the different transmitters are distinguished based on the transmitted characteristics.

In act 36, an angular position of the imaging plane of a transducer array of one of the probes associated with either transmission or reception is determined as a function of a receive signal. The angular position of the imaging plane relative to a probe that includes the transducer imaging array is determined in one embodiment. In another embodiment, the angular position of the imaging plane relative to a probe spaced from the probe having a transducer array for imaging is determined.

The angular position of the imaging plane is determined as a function of ultrasound signals. For example, time-of-flight, signal strength, frequency response or combinations thereof are used to determine the angular position. Where an array of transducer elements are associated with transmitting or reception, the time-of-flight and/or signal strength may be used to determine an angular position or shortest distance between different probes. The frequency content may be used to determine the angular position based on the structure or general shape of the transmit or receive antennas. Where a plurality of antennas associated with a similar shape or variation in shape are provided, relative phasing of transmit signals may be used to determine the angular position based on the frequency content of the receive signals.

The angular position of the imaging plane relative to a probe is determined as a function of a transponder signal strength in other embodiments. Alternatively, timing associated with a radio frequency signal is used. A transponder response to an interrogating signal may be used to determine a transponder distance. Alternatively or additionally, relative signal strength or time-of-flight from a plurality of transponders is used to determine position or angle information.

Further position information with respect to the imaging plane, such as a further angle and/or relative translation of the imaging plane 18 may be determined from other signals. For example, signals are received at a plurality of locations along a lateral or azimuth extent of the array 16. The relative position of an antenna spaced from the array with respect to the imaging plane is determined. Using the relative translation or lateral position as well as the angle along the elevation or perpendicular to lateral dimension of the array allows positioning of the imaging plane to scan the desired location of interest, such as an antenna associated with transmission or reception.

FIG. 7 shows one embodiment of a method for determining a position of an imaging plane relative to a catheter or probe. Additional, different or fewer acts may be provided in alternative embodiments. The method is implemented using the system 10 described with respect to FIGS. 1A and 1B or a different system. The angular position of the imaging plane relative to a catheter is determined as a function of a difference in positions of the probe or catheter, such as based on bending the catheter.

In act 40, the relative position of two or more catheters is determined with groups of acoustic elements. For example, three or more acoustic elements are spaced along each of the catheters (see FIG. 9). By transmitting from one acoustic element of one group and receiving at acoustic elements of another group on a different catheter and repeating the process with further elements of either of the groups of elements, a position of the acoustic elements is determined. The time-of-flight information may be used as disclosed in U.S. Pat. No. 6,490,474 to determine the relative positions within a three-dimensional volume of the various acoustic elements and associated catheters.

In act 42, the tip or other portion of a catheter is bent or changed after determining the relative positions. For example, one or more of the acoustic elements is positioned on the tip or adjacent to another catheter location being changed. Where the catheter may be bent in a known direction relative to an imaging array, the bending of the catheter is provided in a known direction relative to the imaging plane. The imaging plane may be spaced from the bend portion or included on part of the bend portion.

In act 44, the relative position of the catheters is determined again after bending of the catheter associated with the imaging array. The transmission and reception of the various acoustic elements with the tip or other portion of the catheter being in a different position, such as associated with a more straightened position of the catheter or a bent position of the catheter, is provided.

In act 46, the position of the imaging plane is determined as a function of the relative positions. The difference in the relative positions is due to the bending of the catheter associated with the transducer array and imaging plane. Given the known spatial relationship between the induced bend and the imaging plane, such as bending a tip of a catheter within a substantially same plane as the imaging plane to or away from the scan region allows determination of the angular orientation of the imaging plane or scan region relative to the catheter. The determined angular information is used to position a different catheter or device within the imaging plane or to position the imaging plane to scan the different device and/or tissue of interest. More efficient placement of surgical devices and imaging of tissue is provided, allowing for more rapid and efficient performance of surgical procedures using catheter or other intra-patient probes.

FIG. 8 shows a method of one embodiment for using position information for imaging. Additional, different or fewer acts may be provided. The method is implemented using the system 10 discussed above, the system of FIG. 9 or a different system.

In act 50, the relative position of catheters is determined with groups of acoustic elements 24 (see FIG. 9). As shown in FIG. 9, two or more catheters 12, 14 are provided with groups of acoustic elements 24. The acoustic elements 24 are spaced apart along the catheters 12, 14. Additional catheters, additional elements, catheters 12, 14 with different numbers of elements 24, fewer elements 24 or combinations thereof may be used. Since the elements 24 are on different catheters 12, 14, the elements 24 are spaced apart within a patient. Since the elements are spaced apart along each catheter as well, further distribution of the elements 24 is provided. Using the technique described above with respect to act 40 in FIG. 7 or other methods described in U.S. Pat. No. 6,490,474, the relative position of the catheters and associated elements 24 with respect to each other is determined. Alternatively, the relative positions within a three-dimensional volume of the elements 24 with respect to each other are determined. Time-of-flight information may be used to determine the relative position of elements 24 on a same catheter with respect to each other. Time-of-flight information may also be used to determine the relative position of elements 24 of one catheter relative to elements of another catheter 12, 14.

In act 52, an ultrasound image of tissue is generated using the groups of acoustic elements 24. In addition to or as an alternative to using a transducer array, such as an array associated with wavelength or half wavelength spacing of elements, the distributed elements 24 used for determining the relative positions of catheters are also used for imaging. Since the relative positions of the elements 24 with respect to each other are determined, corresponding time delays for imaging may be calculated. Using the same transmit and receive signals for determining relative position or subsequent transmitted and received signals, beamformation is used to generate an ultrasound image of tissue 26 surrounding or adjacent to the catheters 12, 14 based on the calculated time-of-flight information. In one embodiment, a three-dimensional representation is generated. The three-dimensional representation includes one or more of the catheters 12, 14 and/or corresponding elements 24. Three-dimensional representation is of the tissue 26. Although image quality may be less than with a transducer array using immediately adjacent elements due to grating lobes or side lobe artifacts, sufficient resolution may be provided for identifying tissues of interest or a catheter position.

An ultrasound transducer array may alternatively or additionally be used for high resolution imaging. For example, the three-dimensional image is used to locate a tissue 26 of interest and a high resolution two-dimensional imaging using an ultrasound transducer array 16 is used for surgical procedures on the tissue 26. The three-dimensional image may provide the relative position information of the catheters with respect to each other and the tissue 26.

In another embodiment shown in FIG. 10, the position of the imaging plane of a catheter or intra-patient probe is determined using an antenna 25 external to or on the outside of the patient. The position of an ultrasound imaging transducer array 16 and associated imaging plane 18 may be used for three-dimensional imaging or reconstruction, such as by determining the relative positions of a sequence of imaging planes. The position information may be used to position the imaging plane relative to other devices or desired tissue, such as indicating the position of the imaging plane and/or intra-patient probe on a graphic display or three-dimensional representation. The position of a surgical device, such as the catheter 14, may also be determined using antennas 25 external to the patient.

A plurality of antennas 25 are electromagnetic or acoustic antennas. The antennas 25, such as three or more spaced apart antennas 25, are distributed around the patient, such as on the skin of the patient. The antennas 25 are at known positions. In one embodiment, the antennas 25 are omni-directional, but directional antennas 25 may be used. The antennas 25 act as beacons that are interfaced with the processor 17.

The processor 17 is operable to determine angular position information of the imaging plane relative to one of the intra-patient probe or the antennas 25 as a function of a signal of the first antenna 25. Either the ultrasound transducer array or the antennas 25 are used for transmission, and the other of the antennas 20 and the ultrasound transducer array are used for reception. By using the antennas 25 for transmission and the ultrasound imaging transducer array for reception, the receive beamformer may be used for measuring the time-of-flight and/or signal strength. Different transmitters may be distinguished from each other for determining the distance by timing or coding, such as using different frequencies, modulation, number of bursts, number of cycles or type of waveform.

The time-of-flight between the devices is used to determine a distance. By measuring the distance between the end elements, all elements or other elements of the transducer array and the antennas 25, the azimuthal orientation or position of the array in three-dimensions is determined. The position corresponds to a straight or curved line. The elevation orientation or angle of the imaging plane relative to the line is determined by the curve. Alternatively, the angle for a linear array is determined by the signal strength of the received signals. Signals received in a direction more in line with the imaging plane are more likely stronger signals. By meauring absolute or relative signal strengths, the position of the ultrasound imaging transducer array within the patient is determined.

The controller 17 is connected with the imaging system to trigger position determination where the position determination may interfere with imaging. For example, the position determination uses ultrasound frequencies similar or the same as used for imaging. Periodically, such as between every frame or groups of imaging frames of data, the position is determined.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for determining a position of an imaging plane relative to a catheter, the system comprising:
   a first catheter having an ultrasound imaging transducer array, the ultrasound imaging transducer array corresponding to the imaging plane;
   a second catheter having a first antenna, the second catheter at least in part different than the first catheter; and
   a processor operable to determine angular position information of the imaging plane relative to one of the first catheter, the second catheter and combinations thereof as a function of a first signal of the first antenna;
   wherein the first catheter comprises a second antenna positioned relative to the ultrasound imaging transducer array, and wherein the processor is operable to determine the angular position information of the imaging plane as a function of a second signal of the second antenna;
   wherein the second antenna has a variable thickness as a function of angle around the first catheter.

2. The system of claim 1 wherein the first signal is a transmit signal and the second signal is a receive signal responsive to the first signal.

3. The system of claim 1 wherein the first catheter further comprises a third antenna having a variable thickness as a function of angle around the first catheter, the third and second antennas curving as a function of length in a same plane substantially perpendicular to a longitudinal axis of the first catheter.

4. The system of claim 1 wherein the processor is operable to determine a position of the imaging plane relative to the second catheter.

5. The system of claim 1 further comprising at least third and fourth antennas on the first catheter, the second, third and fourth antennas being acoustic elements separate from the ultrasound imaging transducer array, wherein the processor is operable to determine angular position information of the imaging plane relative to the first catheter as a function of signals of the second, third and fourth antennas.

6. The system of claim 1 wherein the second antenna is a separate device integrated on a same substrate as the ultrasound imaging transducer array.

7. The system of claim 1 wherein the processor is responsive to the first and second signals and at least one signal from the ultrasound imaging transducer array to determine the angular position information.

8. The system of claim 1 wherein the processor is operable to determine the angular position information as a function of different positions of the first catheter and the second antenna on the first catheter.

9. The system of claim 1 wherein the first and second catheters comprise intra-cardiac catheters.

10. The system of claim 1 wherein the first signal corresponds to a transmission between the first and second catheters.

* * * * *